United States Patent [19]

Rozzell, Jr.

[11] Patent Number: 5,916,786
[45] Date of Patent: Jun. 29, 1999

[54] METHOD FOR THE PRODUCTION OF CHIRAL 1,3-AMINOALCOHOLS

[75] Inventor: J. David Rozzell, Jr., Burbank, Calif.

[73] Assignee: BioCatalytics, Inc., Burbank, Calif.

[21] Appl. No.: 08/994,163

[22] Filed: Dec. 19, 1997

[51] Int. Cl.$^6$ ..................................... C12P 7/02
[52] U.S. Cl. .................. 435/155; 435/189; 435/190; 435/191; 564/463
[58] Field of Search .................... 435/191, 155, 435/190, 189; 564/463

[56] References Cited

U.S. PATENT DOCUMENTS 3,668,199  6/1972  Szmuskovicz .
5,200,561  4/1993  Konya et al. .

OTHER PUBLICATIONS

1948 J.H. Saunders and R.J. Slocombe, Chem. Rev., 43, pp. 203–218.
1971 D.V. Banthorpe in "The Chemistry of The Azido Group," Chapter 7, pp. 397–405.
1980 J.D. Warren and J.B. Press, Synth. Comm., 10, pp. 107–110.
1969 P.A.S. Smith, Trans. N.Y.Acad. Sci. 31, pp. 504–515.
1973 S. Simons, Jr. J. Org Chem., 38 pp. 414–416.
1976 W.L.F. Amarego et al, J. Chem. Soc. Perkin Trans. I, 2229–2237.
1974 S. Bittner et al, Tetrahedron Letters, 23 pp. 1965–1968.
1974 L. Bauer and O. Exnor, Argew. Chem. Int. Edition, 13, pp. 376–384.
1946 P.A.S. Smith, Organic Reactions III, Chapter 9, pp. 337–338.
1980 Z. Shaked and G. Whitesides, J. Am. Chem. Soc. 102, 7104–7105.
1984 J. B. Jones and T. Takamura, Canadian Journal of Chemistry, 62, 77–80.
1949 E.S. Wallis and J. Flane, Organic Reactions III, Chapter 7, pp. 267–306.
1975 M. Fétizon et al, Tetrahedron, 31 pp. 171–176.
1985 G.L. Lemière et al, Tetrahedron Letters, 26, pp. 4527–4528.
1986 G.L. Lemière in "Enzymes as Catalysts for Organic Synthesis," pp. 19–34, M. Schneider, Editor.
1979 I. J. Jakovac. and J. B. Jones, J. Org. Chem. 44 pp. 2165–2168.
1985 J. B. Jones and I. J. Jakoac. Org. Synth. Coll. Vol. pp. 406–410.
1992 J. B. Jones and I. J. Jakovac in "Preparative Biotransformations" SM. Roberts, Editor, pp. 311–316.

*Primary Examiner*—Leon B. Lankford, Jr.
*Attorney, Agent, or Firm*—Christie, Parker & Hale, LLP

[57] ABSTRACT

The disclosure describes a method for the preparation of chiral 1,3-aminoalcohols in high optical purity. The method combines the stereoselective oxidation of a 1,4-diol to a gamma-lactone using an alcohol dehydrogenase, the conversion of the gamma-lactone to the corresponding 4-hydroxyamide, 4-hydroxyhydroxamic acid, or 4-hydroxyhydrazide, and stereospecific rearrangement of the 4-hydroxyamide, 4-hydroxyhydroxamic acid, or 4-hydroxyhydrazide to the corresponding chiral 1,3-aminoalcohol.

11 Claims, No Drawings

METHOD FOR THE PRODUCTION OF CHIRAL 1,3-AMINOALCOHOLS

FIELD OF THE INVENTION

This invention relates to a method for the production of chiral 1,3-aminoalcohols.

BACKGROUND AND DESCRIPTION OF THE PRIOR ART

Chiral 1,3-aminoalcohols are important intermediates in the synthesis of various pharmaceutical products and product candidates, yet the preparation of these compounds remains a significant synthetic challenge to chemists. Gaining control over the stereochemistry of chiral centers at both the alcohol and amine (or in the cases in which only the alcohol- or amine- bearing carbon is chiral, a single chiral center) is the key to the production of these important chemical intermediates.

Chiral 1,3-aminoalcohols have potential applications both as pharmaceutically-active compounds, agricultural chemicals, chiral intermediates, and chiral auxiliary agents. For example, U.S. Pat. No. 3,668,199 describes novel 1,3-aminoalcohols having potential applications as anti-diabetic agents and diuretics. In the preparation of these compounds according to the method described in U.S. Pat. No. 3,668,199, a diketone is first converted into a keto-enamine, followed by catalytic hydrogenation of the keto-enamine using a platinum catalyst or similar. This method has the limitation that the 1,3-aminoalcohols are not produced in optically-pure form and the amino group must be a dialkylamine. U.S. Pat. No. 5,200,561 describes a process for producing optically active amines, including aminoalcohols. This method reacts an oxime with a metal borohydride compound complexed to a different optically-active amine. This method is costly, and further, requires that another optically active amine be used to form the borohydride complex in order to produce the desired optically active amine. Classical methods involving the formation of diastereomeric salts may also be employed to produce optically active 1,3-aminoalcohols; these resolution procedures require the use of an optically active acid to form the diastereomeric salt. The maximum theoretical yield in this method is only 50%, and in actual practice the yield is significantly lower. Thus, previously-described methods for the production of 1,3-aminoalcohols have limitations in scope, efficiency, chiral purity, and yield. An efficient method for the production of 1,3-aminoalcohols of high optical purity would facilitate the production of a number of pharmaceutical intermediates and chiral auxiliaries, and would be greatly desired.

SUMMARY OF THE INVENTION

In one embodiment, the present invention is directed to a method for producing chiral 1,3-aminoalcohols which comprises the stereoselective oxidation of a 1,4-diol selected from the group consisting of

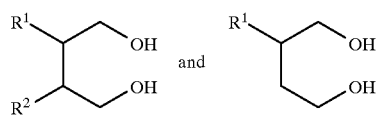

wherein $R^1$ and $R^2$ are independently chosen from the group consisting of alkyl, alkenyl, cycloalkyl, cycloalkylalkyl, cycloalkenyl, cycloalkenylalkyl, alkynyl, aryl, aralkyl, aralkenyl, and heterocyclic ring system, or $R^1$ and $R^2$ together form a cycloalkyl, cycloalkenyl, aryl, or heterocyclic ring system to a chiral gamma-lactone catalyzed by an alcohol dehydrogenase. The resulting chiral gamma-lactone is treated with ammonia, hydroxylamine, or hydrazine under conditions permitting the conversion of the lactone to the corresponding amide, hydroxamic acid, or hydrazide derivative. The resulting 4-hydroxyamide, 4-hydroxyhydroxamic acid, or 4-hydroxyhydrazide is exposed to conditions permitting stereospecific rearrangement to the corresponding chiral 1,3-aminoalcohol. The resulting chiral 1,3-aminoalcohol is optionally recovered.

In another embodiment, the invention is directed to a method for producing esters of chiral 1,3-aminoalcohols which comprises the stereoselective oxidation of a 1,4-diol selected from the group consisting of:

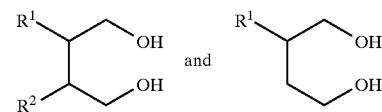

wherein $R^1$ and $R^2$ are independently chosen from the group consisting of alkyl, alkenyl, cycloalkyl, cycloalkylalkyl, cycloalkenyl, cycloalkenylalkyl, alkynyl, aryl, aralkyl, aralkenyl, and heterocyclic ring system, or $R^1$ and $R^2$ together form a cycloalkyl, cycloalkenyl, aryl, or heterocyclic ring system to a chiral gamma-lactone catalyzed by an alcohol dehydrogenase. The chiral gamma-lactone is treated with hydroxylamine under conditions permitting the conversion of the gamma-lactone to the corresponding hydroxamic acid derivative. The resulting 4-hydroxyhydroxamic acid is exposed to conditions of the Lossen rearrangement in which an acyl chloride is used to bring about the stereospecific rearrangement of the hydroxamic acid, producing an ester of a chiral 1,3-aminoalcohol. The ester of the chiral 1,3-aminoalcohol is optionally recovered.

In still another embodiment, the invention is directed to a method for producing chiral 1,3-aminoalcohols which comprises producing an ester of a chiral 1,3-aminoalcohol using the method described above and hydrolyzing the ester.

DETAILED DESCRIPTION OF THE INVENTION

This invention provides an efficient method for the production of chiral 1,3-aminoalcohols. An important aspect of this invention is the generality with which this method described herein may be employed to produce a range of chiral 1,3-aminoalcohols, both cyclic and acydic, in high stereochemical purity. The method of the present invention may be used in cases where both the carbon atom bearing the amino group and the carbon atom bearing the hydroxy group are chiral, or alternatively, in cases where only the carbon bearing the amino group or the carbon bearing the hydroxy group is chiral.

Central to this invention is the novel combination of three steps, each of which proceeds with a well-defined and controllable stereochemical outcome. The first step is the stereoselective oxidation of a 1,4-diol to the corresponding chiral gamma-lactone using an alcohol dehydrogenase. The 1,4-diol used in the practice of the present invention is preferably substituted at the 2-position or at both the 2- and 3-positions as shown in FIGURE 1.

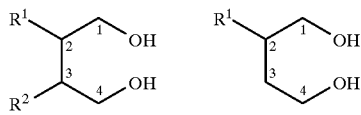

Figure 1: Structures of 1, 4-Diols

The substitution is represented in the figure by $R^1$ and $R^2$, which may be selected independently from the substituent groups alkyl, alkenyl, cycloalkyl, cycloalkenyl, cycloalkylalkyl, cydoalkenylalkyl, alkynyl, aryl, aralkyl, and heterocyclic ring system. $R^1$ and $R^2$ may also together form a cydoalkyl, cydoalkenyl, or heterocyclic ring system, for example, as in the compound 1,2-cyclohexane dimethanol or 1,2-cydopentane dimethanol. In cases where $R^1$ and $R^2$ are identical and the diol is a meso compound, the yield of the resulting 1,3-aminoalcohol produced by the method of the present invention can approach 100% of theoretical.

As utilized herein, the term "alkyl," alone or in combination, means a straight-chain or branched-chain alkyl group containing from 1 to about 12 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of such alkyl groups include methyl, ethyl, chloroethyl, propyl, isopropyl, butyl, isobutyl, tertiary-butyl, 3-fluorobutyl, 4-nitrobutyl, 2,4-dibromobutyl, pentyl, isopentyl, neopentyl, 3-ketopentyl, hexyl, 4-acetamidohexyl, 3-phosphonoisohexyl, 4-fluoro-5,5-dimethylpentyl, 5-phosphinoheptyl, octyl, nonyl, dodecyl, and the like.

As utilized herein, the term "alkenyl," alone or in combination, means a straight-chain or branched-chain hydrocarbon group containing one or more carbon-carbon double bonds and containing from 2 to about 18 carbon atoms. Any of the carbon atoms may be substituted with one or more substituents selected from alkoxy, acyloxy, acylamido, halogen, nitro, sulfhiydryl, sulfide, carboxyl, oxo, seleno, phosphate, phosphonate, phosphine, and the like. Examples of such alkenyl groups include ethenyl, propenyl, allyl, 1,4-butadienyl, 2-pentenyl, 3-pentenyl, 4-pentenyl, 2,6-decadienyl, 2-fluoropropenyl, 2-methoxypropenyl, 2-carboxypropenyl, 3-chlorobutadienyl, and the like.

As utilized herein, the term "cycloalkyl," alone or in combination, means an alkyl group which contains from about 3 to about 12 carbon atoms and is cyclic. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of cydoalkyl groups include cyclopropyl, cydobutyl, cydopentyl, cydohexyl, cydoheptyl, 2-methylcyclopentyl, 3-methylcydohexyl, various substituted derivatives, and the like.

As utilized herein, the term "cycloalkenyl," alone or in combination, means an alkenyl group which contains from about 3 to about 12 carbon atoms and is cyclic. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of cycloalkyl groups include cyclopropenyl, cyclobutenyl, cyclopentenyl, cydohexenyl, cyclohexadienyl, cydoheptenyl, 2-methylcydopentenyl, 3-methylcyclohexenyl, 3-chlorocydohexenyl, 3-carboxymethylcyclopentenyl, and the like.

As utilized herein, the term "cycloalkylalkyl," alone or in combination, means an alkyl group as defined above which substituted by a cycloalkyl group containing from about 3 to about 12 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of cycloalkyl groups include cydopropyl, cydobutyl, cyclopentyl, cyclohexyl, cycloheptyl, 2-methylcyclopentyl, 3-methylcyclohexyl, 3-fluoromethylcyclohexyl, 3-carboxymethylcyclohexyl, 2-chloro-3-methylcyclopentyl, and the like.

As utilized herein, the term "cycloalkenylalkyl," alone or in combination, means an alkyl group as defined above which is substituted with a cydoalkenyl group containing from about 3 to about 12 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of cydoalkyl groups include cydopropenyl, cydobutenyl, cydopentenyl, cyclohexenyl, cydoheptenyl, 2-methylcydopentenyl, 3-methylcyclohexenyl, 3-fluoromethylcyclohexenyl, 3-carboxymethylcyclohexenyl, 2-chloro-3-methylcyclopenentyl, 3-nitrocydohexenyl, and the like.

As utilized herein, the term "alkynyl," alone or in combination, means a straight-chain or branched-chain hydrocarbon group containing one or more carbon-carbon triple bonds and containing from 2 to about 18 carbon atoms. Any of the carbon atoms may be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of such alkenyl groups include ethynyl, propynyl, 1,4-butadiynyl, 3-pentynyl, 2,6-decadiynyl, 2-fluoropropynyl, 3-methoxy-1-propynyl, 3-carboxy-2-propynyl, 3-chlorobutadiynyl, and the like.

As utilized herein, the term "aryl," alone or in combination, means a carbocydic aromatic system containing 1, 2, or 3 rings, wherein such rings may be attached in a pendent manner to each other or may be fused to each other. Examples of aryl groups include phenyl, naphthyl, biphenyl, and the like, which may optionally be substituted with one or more substituents selected from the group consisting of alkoxy, acyloxy, acylamido, halogen, nitro, sulfhydryl, sulfide, carboxyl, oxo, seleno, phosphate, phosphonate, phosphine, and the like. Examples of such aryl groups include phenyl, 4-fluorophenyl, 2-chloroethyl, 3-propylphenyl, 1-naphthyl, 2-naphthyl, 2-methoxy-1-naphthyl, 3,4-dimethoxyphenyl, 2,4-difluorophenyl, and the like.

As utilized herein, the term "aralkyl," alone or in combination, means an alkyl group as defined above which is substituted with an aryl group. Examples of aralkyl groups include benzyl, 2-phenylethyl, 2,4-dimethoxybenzyl, 4-fluorobenzyl, 4-chlorobenzyl, 4-bromobenzyl, 4-iodobenzyl, and the like.

As utilized herein, the term "heterocyclic ring system," alone or in combination, means a saturated or partially unsaturated monocyclic, bicyclic, or tricyclic group containing one or more heteroatoms as ring atoms, said heteroatoms selected from oxygen nitrogen, sulfur, phosphorous, selenium, and silicon. Any of the carbon atoms in the heterocycle may be optionally substituted with one or more substituents selected from the group consisting of alkoxy, acyloxy, acylamido, halogen, nitro, sulffiydryl, sulfide, carboxyl, oxo, seleno, phosphate, phosphonate, phosphine, and the like. Examples of such heterocyclic ring systems include imidazoyl, oxazolinyl, piperazinyl, pyrollidinyl, phthanmidoyl, maleimidyl, thiamorpholinyl, various substituted derivatives, and the like.

The oxidation of the 1,4-diol to the corresponding chiral gamma-lactone occurs by way of formation of the intermediate lactol, which is further oxidized by the alcohol dehydrogenase to the lactone. Some examples of oxidation of 1,4-diols to the corresponding chiral lactones catalyzed by horse liver alcohol dehydrogenase is described in J. B. Jones and I. J. Jakovac, *J. Org. Chem.*, 44, 2165 (1979); J. B. Jones and I. J. Jakovac, *Org. Synth.* 63, 10 (1985); and Preparative *Biotransformations* (S. M. Roberts, editor), Chapter 3, pages 3.1.1–3.1.6, John Wiley & Sons, Chichester, U.K. (1997), all hereby incorporated by reference.

In some cases the intermediate chiral lactol may be isolated and oxidized chemically to the gamma-lactone. One method for effecting this oxidation uses silver carbonate on Celite as the oxidizing agent; this method is described by Fétizon et al in *J. Chem Soc. Chem Comm.*, 1118 (1969) and *Tetrahedron*, 31, 171 (1975), both hereby incorporated by reference.

Alcohol dehydrogenases used in the practice of this invention require cofactors such as nicotinamide adenine dinudeotide (NAD+) or nicotinamide adenine dinucleotide phosphate (NADP+). A requirement for carrying out the oxidation of a 1,4-diol to the corresponding chiral gamma-lactone at a reasonable cost is the recycling of the NAD+ or NADP+ cofactor. Numerous methods for the recycling of these cofactors are well-known in the art, and any of these methods may be used in the practice of this invention. Some of the methods for recycling NAD+ and NADP+ cofactors are described in G. L. Lemiere, J. A. Lepoivre, and F. C. Alderweireldt, *Tetrahedron Letters*, 26,4257 (1985); in "Enzymes as Catalysts for Organic Synthesis," pp. 19–34, M. Schneider, Ed., Reidel Dordecht, 1986; Z. Shaked and G. M. Whitesides, *J. Am. Chem. Soc.* 102, 71045 (1980); J. B. Jones and T. Takarnura, *Can. J. Chem.* 62, 77 (1984); all hereby incorporated by reference. all hereby incorporated by reference. A recycling method described in *Preparative Biotransformations* (S. M. Roberts, editor), Chapter 3, pages 3.1.1–3.1.6, John Wiley & Sons, Chichester, U.K. (1997) uses flavin mononucleotide (FMN), which transfers electrons to oxygen as the ultimate oxidant. In the use of this method, an amount of about 0.0005 moles to about 0.05 moles of NAD+ or NADP+ is used per mole of diol to be oxidized, providing a recycle number for the cofactor of from about 20 to about 2000.

Some alcohol dehydrogenases useful in the practice of this invention include yeast alcohol dehydrogenase, horse liver alcohol dehydrogenase, bacterial alcohol dehydrogenase from *Thermoanaerobium brockii*, bacterial alcohol dehydrogenase from *Lactobacillus kefir*, alcohol dehydrogenases sold under the ThermoCat trademark by ThermoGen, Inc., and many others. By using alcohol dehydrogenases with differing substrate ranges and different stereoselectivity, different stereoisomers of chiral gamma-lactones may be produced. For example, the alcohol dehydrogenase from *Lactobacillus kefir* (Sigma) has the opposite stereoselectivity from horse liver alcohol dehydrogenase (Sigma, Boehringer Mannheim).

In accord with this invention, oxidation of a 1,4-diol to the corresponding chiral gamma lactone may be conveniently carried out using isolated alcohol dehydrogenase enzymes or using whole cells containing alcohol dehydrogenases enzymes. In the case where isolated alcohol dehydrogenase enzymes are used, these enzymes may be used either as crude, partially purified, or pure preparations. Alcohol dehydrogenases useful in the practice of this invention may be isolated and purified, if desired, from microorganisms capable of effecting the stereoselective oxidation. The purification of the dehydrogenase enzymes may be accomplished by techniques well known to those skilled in the art. Some examples of purification methods for enzymes may be found in *Methods in Enzymology*, 22 (1971) and references therein, hereby incorporated by reference.

These enzymes may be used in solution or, if desired, as immobilized enzymes in accord with the practice of this invention. A number of methods of immobilization for both whole cells containing enzymes and for isolated enzymes are known in the prior art and may be used in the practice of this invention. One example of an immobilized enzyme system is described by Weetall et al., *Methods in Enzymology* 34, 59–72 (1974) which is hereby incorporated by reference. In this method enzymes may be immobilized on a porous glass or ceramic support which has been activated with glutaraldehyde. Other methods for immobilization of both cells and enzymes which may be used in the practice of this invention are described in *Methods in Enzymology* 44 (1976), K. Mosbach editor, *Immobilization of Enzymes and Cells*, Gordon F. Bickerstaff, ed., Humana Press, Totowa, N.J. (1997) and in *Biocatalytic Production of Amino Acids and Derivatives*, D. Rozzell and F. Wagner, Eds., Hanser Publishers, Munich, (1992) pp. 279–319.

When whole cells containing alcohol dehydrogenases enzymes are used to catalyze the oxidation of a 1,4-diol to the corresponding chiral gamma-lactone, the addition of a cofactor is not required, as the cell supplies the necessary cofactor. Commonly, when whole cells are used in the practice of this invention, a carbon source such as glucose is added to the medium to supply energy to the cell for maintenance and regeneration of the cofactor. Cells useful in the practice of this invention include the same organisms from which useful alcohol dehydrogenases may be isolated, including Baker's yeast, *Lactobacillus kefir, Thermoanaerobium brockii*, and many other microorganisms which produce an alcohol dehydrogenase.

The second step in the method of the present invention is the treatment of the chiral gamma-lactone with hydrazine, hydroxylamine, or ammonia under conditions permitting the formation of the corresponding 4-hydroxycarboxamide, 4-hydroxyhydroxamic add, or 4-hydroxyhydrazide. Conversion of the chiral gamma-lactone to its 4hydroxyamide, 4hydroxyhydroxamic acid or 4hydroxyhydrazide derivative may be accomplished by straightforward chemical methods well known to those skilled in the art. For example, heating of a chiral gamma-lactone with ammonia, hydrazine, or hydroxylamine in ethanol produces the corresponding amide, hydrazide, or hydroxamic add in high yield, and without affecting the chirality at the carbon bearing the carboxyl group. Alternatively, conversion of the gamma-lactone to the amide, hydroxamic acid or hydrazide may be accomplished by enzymatic catalysis. Esterase, lipase, protease, and amidase enzymes, which can catalyze the hydrolysis of esters in the presence of water, will catalyze conversion of the ester to the amide, hydroxamic acid or hydrazide when ammonia, hydroxylamine or hydrazine are present as nucleophiles. The enzymatic conversion has the added advantage that it often can be carried out under very mild conditions (e.g. ambient temperature and pressure). Further, in certain cases, the enzyme can provide additional stereoselectivity, if desired, in the conversion of the gamma-lactone to its corresponding amide, hydroxamic acid or hydrazide derivative, further improving the enantiopurity of the final product. Some esterases and lipases useful in the conversion of a chiral gamma-lactone to its amide, hydroxamic acid, or hydrazide derivative include *Candida antarctica* lipase (Boehringer Mannheim), *Candida rugosa* lipase (Amano), *Mucor mehei* lipase (Boehringer Mannhiem), esterases sold under the ThermoCat trademark by ThermoGen, Inc., esterases sold by Diversa, various proteases sold by Sigma and Boehringer Mannheim, and many others. These esterases, lipases, amidases, and proteases may also be immobilized as described for the alcohol dehydrogenases using methods well known in the art, if desired.

The third step in the method of the present invention is the stereospecific conversion of the resulting 4-hydroxycarboxamide, 4-hydroxyhydrazide, or 4-hydroxyhydroxamic acid to the corresponding 1,3-aminoalcohol. This conversion may be carried out on the amide under conditions described for the Hofmann Rearrangement, on the hydroxamic acid under conditions described for the Lossen rearrangement, and on the hydrazide under conditions described for the Curtius Rearrangement. These rearrangements are well known in the art. In particular, the stereochemical course of these rearrangements has been well studied, and they have been shown to take place with retention of stereochemistry at the carbon bearing the carbonyl group.

The stereospecific rearrangement may be carried out on the carboxamide via the Hofmann rearrangement [E. S. Wallis and J. F. Lane, *Organic Reactions* III, 267 (1949) and references therein; P. A. S. Smith, *Trans. N.Y. Acad. Sci.* 31, 504 (1969) and references therein; S. Simons, *J. Org Chem.* 38, 414 91973) and references therein; W. L. F. Armarego et al, *J. Chem. Soc. Perkin Trans.* I, 2229 (1976) and references therein; all hereby incorporated by reference]; on the hydroxamic acid via the Lossen rearrangement [S. Bittner et al (*Tet. Lett.* 23, 1965–8 (1974) and references therein; L. Bauer and O. Exner, *Angew. Chem. Int. Ed.* 13, 376 (1974) and references therein; all hereby incorporated by reference]; or on the hydrazide via the Curtius rearrangement [P. A. S. Smith, *Organic Reactions* III, 337 (1946) and references therein; J. H. Saunders and R. J. Slocombe, *Chem. Rev.* 43,205 (1948) and references therein; D. V. Banthorpe in *The Chemistry of the Azido Group,* S. Patai Ed., Interscience, New York, 1971, pp. 397–05 and references therein; J. D. Warren and J. D. Press, *Synth. Comm.* 10, 107 (1980) and references therein; all hereby incorporated by reference]. When an acyl halide or similar is used to activate the N-hydroxy group in the Lossen rearrangement, acylation of the alcohol also occurs, producing an ester of the chiral 1,3-aminoalcohol. The ester may be hydrolyzed, if desired, to the corresponding chiral 1,3-aminoalcohol by methods well known in the art.

In cases where either the carbon bearing the alcohol or the carbon bearing the carboxyl group is the only chiral center, the sequence is similarly effective, maintaining complete control over the chirality at the chiral center after through the rearrangement of the amide, hydrazide, or hydroxamic acid.

When meso-diols are used as the starting material for the method of the present invention, a single stereoisomer of a chiral 1,3-aminoalcohol can be obtained in yields approaching 100% of theoretical. For example, cis-1,2-cydohexane dimethanol is converted into (1S,2R)-1-amino-2-(hydroxymethyl)cyclohexane and meso-2,3-dimethyl 1,4-butanediol is converted into (2S,3S)-2-methyl-3-aminobutan-1-ol.

The invention will now be further described by the following examples, which are given here for illustrative purposes only and are not intended to limit the scope of the invention.

EXAMPLE 1

Oxidation of cis-1,2-cyclohexane dimethanol to (1R,6S)-(+)-8-oxabicyclo[4.3.0]nonan-7-one Glycine (18.8 grams) is dissolved in 2 liters of deionized water, and the pH is adjusted by the addition of 10% sodium hydroxide to 9.0. Cis-1,2-cyclohexane dimethanol (10.0 grams) is added to the glycine solution with stirring until dissolution occurs, followed by the addition of βNAD+ (Sigma, 2 grams) and flavin mononucleotide (Sigma, 30 grams). To the resulting dear orange solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (1R,6S)-(+)-8-oxabicylo[4.3.0]nonan-7-one (9 grams) as an orange oil. The product may be further purified by distillation at reduced pressure to yield a colorless oil, $[\partial]_D=+46°$ c=1.1, chloroform. The enantiomeric excess is 98% as determined by chiral gas chromatography (Lipodex D column, column temperature 165° C., injection temperature 180° C., detector temperature 260° C.).

EXAMPLE 2

Alternative oxidation of cis-1,2-cyclohexane dimethanol to (1R,6S)-(+)-8-oxabicyclo[4.3.0] nonan-7-one Glycine (18.8 grams) is dissolved in 2 liters of deionized water, and the pH is adjusted by the addition of 10% sodium hydroxide to 9.0. Cis-1,2-cyclohexane dimethanol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (1R,6S)-(+)-8-oxabicyclo[4.3.0]nonan-7-one (8.5 grams) as a yellowish oil.

EXAMPLE 3

Oxidation of meso-2,3-dimethyl-1,4-butanediol to (2S,3R)-2,3-dimethylbutyrolactone Glycine (18.8 grams) is dissolved in 2 liters of deionized water, and the pH is adjusted by the addition of 10% sodium hydroxide to 9.0. Cis-1,2-cyclohexane dimethanol (10.0 grams) is added to the glycine solution with stirring until dissolution occurs, followed by the addition of β-NAD+ (Sigma, 2 grams) and flavin mononudeotide (Sigma, 30 grams). To the resulting dear orange solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by extraction with ethyl acetate (4 times 250 ml). The ethyl acetate extract is dried over anhydrous magnesium sulfate and evaporated under reduced pressure to yield (2R,3S)-2,3-dimethylbutyrolactone (9 grams) as an orange oil.

EXAMPLE 4

Alternative oxidation of meso-2,3-dimethyl-1,4-butanediol to (2S,3R)-2,3-dimethylbutyrolactone Glycine (18.8 grams) is dissolved in 2 liters of deionized water, and the pH is adjusted by the addition of 10% sodium hydroxide to 9.0. 2,3-Dimethyl-1,4-butanediol (10.0 grams) is dissolved in 150 ml of acetone added to the glycine solution with stirring, followed by the addition of βNAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R, 3S)-2, 3-dimethylbutyrolactone (8 grams) as a yellowish oil.

EXAMPLE 5

Oxidation of cis-1,2-cyclopentane dimethanol to (1R,5S)-(+)-7-oxabicyclo[3.3.0]octan-6-one Glycine (18.8 grams) is dissolved in 2 liters of deionized water, and the pH is adjusted by the addition of 10% sodium hydroxide to 9.0. Cis-1,2-cydopentane dimethanol (10.0 grams) is added to the glycine solution with stirring until dissolution occurs, followed by the addition of β-NAD+ (Sigma, 2 grams) and flavin mononucleotide (Sigma, 30 grams). To the resulting dear orange solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (1R,5S)-(+)-7-oxabicyclo[3.3.0]octan-6-one (9 grams) as an orange oil. The product may be further purified by distillation at reduced pressure to yield a colorless oil.

EXAMPLE 6

Alternative oxidation of cis-1,2-cyclopentane dimethanol to (1R,5S)-(+)-7-oxabicyclo[3.3.0] octan-6-one Glycine (18.8 grams) is dissolved in 2 liters of deionized water, and the pH is adjusted by the addition of 10% sodium hydroxide to 9.0. Cis-1,2-cydopentane dimethanol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent 1:1 ethyl acetate-methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (1R,5S)-(+)-7-oxabicyclo[3.3.0]nonan-6one (8 grams) as a yellowish oil.

EXAMPLE 7

Production of (R)-2-phenylbutyrolactone by oxidation of 2-phenyl-1,4-butanediol

Glycine (18.8 grams) is dissolved in 2 liters of deionized water, and the pH is adjusted by the addition of 10% sodium hydroxide to 9.0. 2-Phenyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (R)-2-phenylbutyrolactone as a yellowish solid.

EXAMPLE 8

Production of (R)-2-benzylbutyrolactone by oxidation of 2-benzyl-1,4-butanediol

Glycine (18.8 grams) is dissolved in 2 liters of deionized water, and the pH is adjusted by the addition of 10% sodium hydroxide to 9.0. 2-Benzyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (R)-2-benzylbutyrolactone as a yellowish solid.

EXAMPLE 9

Production of (2R)-2-(3-fluoropropyl)butyrolactone by oxidation of 2-(3-fluoropropyl)-1,4-butanediol Glycine (18.8 grams) is dissolved in 2 liters of deionized water, and the pH is adjusted by the addition of 10% sodium hydroxide to 9.0. 2-(3-fluoropropyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(3-fluoropropyl)butyrolactone as a yellowish oil.

EXAMPLE 10

Production of (2R)-2-imidazoylbutyrolactone by oxidation of 2-imidazoyl-1,4-butanediol Glycine (18.8 grams) is dissolved in 2 liters of deionized water, and the pH is adjusted by the addition of 10% sodium hydroxide to 9.0. 2-Imidazoyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-imidazoylbutyrolactone as a yellowish solid.

EXAMPLE 11

Production of (2R)-2 (4-fluorophenyl)butyrolactone by oxidation of 2-(4fluorophenyl)-1,4-butanediol Glycine (18.8 grams) is dissolved in 2 liters of deionized water, and the pH is adjusted by the addition of 10% sodium hydroxide to 9.0. 2-(4-fluorophenyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(4-fluorophenyl)butyrolactone as a yellowish solid.

EXAMPLE 12

Production of (2R)-2 cydohexylbutyrolactone by oxidation of 2-cyclohexyl-1,4-butanediol Glycine (18.8 grams) is dissolved in 2 liters of deionized water, and the pH is adjusted by the addition of 10% sodium hydroxide to 9.0. 2-Cydohexyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-cydohexylbutyrolactone as a yellowish solid.

EXAMPLE 13

Production of (2R)-2 (4-methoxyphenyl) butyrolactone by oxidation of 2-(4-methoxyphenyl)-1,4-butanediol Glycine (18.8 grams) is dissolved in 2 liters of deionized water, and the pH is adjusted by the addition of 10% sodium hydroxide to 9.0. 2-(4-methoxyphenyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(4-methoxyphenyl)butyrolactone as a yellowish solid.

EXAMPLE 14

Production of (2R)-2 (3,4-dimethoxyphenyl) butyrolactone by oxidation of 2-(3,4-dimethoxyphenyl)-1,4-butanediol Glycine (18.8 grams) is dissolved in 2 liters of deionized water, and the pH is adjusted by the addition of 10% sodium hydroxide to 9.0. 2-(3,4-dimethoxyphenyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(3,4-dimethoxyphenyl)butyrolactone as a yellowish solid.

EXAMPLE 15

Production of (2R)-2 (4-carboxyphenyl) butyrolactone by oxidation of 2-(4-carboxyphenyl)-1,4-butanediol Glycine (18.8 grams) is dissolved in 2 liters of deionized water, and the pH is adjusted by the addition of 10% sodium hydroxide to 9.0. 2-(4-carboxyphenyl)-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R)-2-(4-carboxyphenyl)butyrolactone as a yellowish solid.

EXAMPLE 16

Oxidation of meso-2,3-bis-carboxymethyl-1,4-butanediol to (2R, 3S)-2,3-bis-carboxymethylbutyrolactone Glycine (18.8 grams) is dissolved in 2 liters of deionized water, and the pH is adjusted by the addition of 10% sodium hydroxide to 9.0. 2,3-bis-carboxymethyl-1,4-butanediol (10.0 grams) is dissolved in 150 ml of acetone added to the glycine solution with stirring, followed by the addition of β-NAD+ (Sigma, 0.5 grams). To the resulting solution is added horse liver alcohol dehydrogenase (Sigma, 250 mg, approximately 400 units). After the enzyme has dissolved the pH is readjusted to 9.0 with 10% sodium hydroxide, and the reaction mixture is stirred at 30° C. During the reaction, the pH is maintained at 9.0 with a pH-stat by the addition of 10% sodium hydroxide. Progress of the reaction is monitored by thin layer chromatography (Silica gel plates, eluent methylene chloride; visualization by dipping in a solution of 5% anisaldehyde in ethanol and heating). When the reaction is complete as judged by thin layer chromatography, the reaction mixture is adjusted to a pH of 13 with 10 M sodium hydroxide and then extracted 3 times with 250 ml of methylene chloride. The pH of the aqueous mixture is then adjusted to 3 with concentrated HCl, followed by continuous extraction with 1 liter of ethyl acetate for 24 hours. The ethyl acetate extract is dried over anhydrous magnesium sulfate and evaporated under reduced pressure to yield (2R, 3S)-2,3-bis-carboxymethylbutyrolactone (8 grams) as a yellowish solid.

EXAMPLE 17

Conversion of (1R,6S)-(+)-8-oxabicyclo[4.3.0] nonan-7-one to (1S,2R)-2-hydroxymethyl-1-cydohexanecarboxylate hydroxamic acid (1R,6S)-(+)-8-oxabicyclo[4.3.0]nonan-7-one (1 gram) was dissolved in 5 ml of absolute ethanol, followed by the addition of 0.5 gram of hydroxylamine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (1S,2R)-2-hydroxymethyl-1-cydohexanecarboxylate.

EXAMPLE 18

Enzymatic production of the hydroxamic add of (1S,2R)-2-hydroxymethyl-1-cyclohexanecarboxylate (1R,6S)-(+)-8-oxabicylo[4.3.0]nonan-7-one (1 gram) was dissolved in 5 ml of t-butyl methyl ether, followed by the addition of 0.5 gram of hydroxylamine. Lipase from Candida rugosa (0.5 g, Sigma L1754) was added, and the progress of the reaction was followed by thin layer chromatography. After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (1S,2R)-2-hydroxymethyl-1-cyclohexanecarboxylate.

EXAMPLE 19

Conversion of (1R,5S)-(+)-7-oxabicylo[3.3.0]octan-6-one to (1S,2R)-2-hydroxymethyl-1-cyclopentanecarboxylic hydroxamic acid (1R,5S)-(+)-7-oxabicyclo[3.3.0]octan-6-one (1 gram) was dissolved in 5 ml of absolute ethanol, followed by the addition of 0.5 gram of hydroxylamine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (1S,2R)-2-hydroxymethyl-1-cyclopentanecarboxylate.

EXAMPLE 20

Enzymatic production of the hydroxamic acid of (1S,2R)-2-hydroxymethyl-1-cyclopentanecarboxylate (1R,5S)-(+)-7-oxabicylo[3.3.0]octan-6-one (1 gram) was dissolved in 5 ml of t-butyl methyl ether, followed by the addition of 0.5 gram of hydroxylamine. Lipase from Candida rugosa (0.5 g, Sigma L1754) was added, and the progress of the reaction was followed by thin layer chromatography. After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (1S,2R)-2-hydroxymethyl-1-cydopentanecarboxylate.

EXAMPLE 21

Conversion of (2S,3R)-2,3-dimethylbutyrolactone to (2S,3R)-2,3-dimethyl-4-hydroxybutanoate hydroxamic acid (2S,3R)-2,3-dimethylbutyrolactone (1 gram) was dissolved in 5 ml of absolute ethanol, followed by the addition of 0.5 gram of hydroxylamine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (2S,3R)-2,3-dimethyl-4-hydroxybutanoate.

EXAMPLE 22

Enzymatic production of the hydroxamic acid of (2S,3R)-2,3-dimethyl-4-hydroxybutanoate (2S,3R)-2,3-dimethylbutyrolactone (1 gram) was dissolved in 5 ml of t-butyl methyl ether, followed by the addition of 0.5 gram of hydroxylamine. Lipase from Candida rugosa (0.5 g, Sigma L1754) was added, and the progress of the reaction was followed by thin layer chromatography. After the reaction was judged complete, the ethanol was evaporated and the resulting residue redissolved in ethyl acetate. Hydroxylamine was removed by extraction with 1% HCl, and the ethyl acetate solution was dried over MgSO$_4$, filtered, and rotary evaporated to leave 0.8 grams of the hydroxamic acid derivative of (2S,3R)-2,3-dimethyl-4-hydroxybutanoate.

EXAMPLE 23

Conversion of (1R,6S)-(+)-8-oxabicyclo[4.3.0] nonan-7-one to the (1S,2R)-2-hydroxymethyl-1-cydohexanecarboxylic hydrazide (1R,6S)-(+)-8-oxabicyclo[4.3.0]nonan-7-one (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/ methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (1S,2R)-2-hydroxymethyl-1-cydohexanecarboxylate.

EXAMPLE 24

Conversion of (1R,5S)-(+)-7-oxabicyclo[3.3.0] octan-6-one to (1S,2R)-2-hydroxymethyl-1-cydopentanecarboxylic hydrazide (1R,5S)-(+)-7-oxabicyclo[3.3.0]octan-6-one (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/ methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (1S,2R)-2-hydroxymethyl-1-cyclopentanecarboxylate.

EXAMPLE 25

Conversion of (2S, 3R)-2,3-dimethylbutyrolactone to (2S,3R)-2,3-dimethyl-4-hydroxybutanoic hydrazide (2S, 3R)-2,3-dimethylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (2S,3R)-2,3-dimethyl-4-hydroxybutanoic acid.

EXAMPLE 26

Conversion of (1R,6S)-(+)-8-oxabicyclo[4.3.0] nonan-7-one to (1S,2R)-2-hydroxymethyl-1-cyclohexanecarboxamide (1R,6S)-(+)-8-oxabicylo[4.3.0]nonan-7-one (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (1S,2R)-2-hydroxymethyl-1-cyclohexanecarboxamide.

EXAMPLE 27

Conversion of (1R,5S)-(+)-7-oxabicyclo[3.3.0] octan-6-one to (1S,2R)-2-hydroxymethyl-1-cyclopentanecarboxamide (1R,5S)-(+)-7-oxabicyclo[3.3.0]octan-6-one (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (1S,2R)-2-hydroxymethyl-1-cydopentanecarboxamide.

EXAMPLE 28

Conversion of (2S,3R)-2,3-dimethylbutyrolactone to the (2S,3R)-2,3-dimethyl-4-hydroxybutyramide (2S,3R)-2,3-dimethylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (2S,3R)-2,3-dimethyl-4-hydroxybutyramide.

EXAMPLE 29

Conversion of (R)-2-phenylbutyrolactone to the (R)-2-phenyl-4-hydroxybutyramide (R)-2-phenylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (R)-2-phenyl-4hydroxybutyramide.

EXAMPLE 30

Conversion of (R)-2-benzylbutyrolactone to the (R)-2-benzyl-4-hydroxybutyramide (R)-2-benzylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (R)-2-benzyl-4-hydroxybutyramide.

EXAMPLE 31

Conversion of (R)-2-phenylbutyrolactone to (R)-2-phenyl-4-hydroxybutanoic acid hydrazide (R)-2-phenylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (R)-2-phenyl-4-hydroxybutanoic acid.

EXAMPLE 32

Conversion of (R)-2-benzylbutyrolactone to (R)-2-benzyl-4-hydroxybutanoic acid hydrazide (R)-2-benzylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (R)-2-benzyl-4-hydroxybutanoic acid.

EXAMPLE 33

Conversion of (R)-2-(4-fluorophenyl)butyrolactone to (R)-2-(4-fluorophenyl)-4-hydroxybutanoic acid hydrazide (R)-2-(4-fluorophenyl)butyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (R)-2-(4-fluorophenyl)-4-hydroxybutanoic acid.

EXAMPLE 34

Conversion of (S)-2-phenylbutyrolactone to the (S)-2-phenyl-4-hydroxybutyramide (S)-2-phenylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (S)-2-phenyl-4-hydroxybutyramide.

EXAMPLE 35

Conversion of (S)-2-benzylbutyrolactone to the (S)-2-benzyl-4-hydroxybutyramide (S)-2-benzylbutyrolactone (1 gram) was dissolved in 5 ml of absolute ethanol, followed by the addition of 0.5 gram of gaseous ammonia. The solution was kept in a stoppered flask, and the progress of the reaction was followed by thin layer chromatography (eluent dichloromethane/methanol 20:1). After the reaction was judged complete, the ethanol was evaporated and the resulting residue redissolved in ethyl acetate. Ammonia was removed by extraction with 1% HCl, and the ethyl acetate solution was dried over MgSO$_4$, filtered, and rotary evaporated to leave 0.7 grams of (S)-2-benzyl-4-hydroxybutyramide.

EXAMPLE 36

Conversion of (S)-2-phenylbutyrolactone to (S)-2-phenyl-4-hydroxybutanoic acid hydrazide (S)-2-phenylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (S)-2-phenyl-4-hydroxybutanoic acid.

EXAMPLE 37

Conversion of (S)-2-benzylbutyrolactone to (S)-2-benzyl-4-hydroxybutanoic acid hydrazide (S)-2-benzylbutyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (S)-2-benzyl-4-hydroxybutanoic acid.

EXAMPLE 38

Conversion of (S)-2-(4-fluorophenyl)butyrolactone to (S)-2-(4fluorophenyl)-4-hydroxybutanoic acid hydrazide (S)-2-(4-fluorophenyl)butyrolactone (1 gram) was dissolved in 5 ml of absolute ethanol, followed by the addition of 0.5 gram of hydrazine. The solution was heated to reflux, and the progress of the reaction was followed by thin layer chromatography (eluent dichloromethane/methanol 20:1). After the reaction was judged complete, the ethanol was evaporated and the resulting residue redissolved in ethyl acetate. Hydrazine was removed by extraction with 1% HCl, and the ethyl acetate solution was dried over MgSO$_4$, filtered, and rotary evaporated to leave 0.9 grams of the hydrazide of (S)-2-(4-fluorophenyl)-4-hydroxybutanoic acid.

EXAMPLE 39

Production of (1S,2R)-1-amino-2-(hydroxymethyl) cydohexane by Hofmann Rearrangement of (1S,2R)-2-hydroxymethyl-1-cyclohexanecarboxamide Ten grams of (1S,2R)-2-hydroxymethyl-1-cyclohexanecarboxamide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (1S,2R)-1-amino-2-(hydroxymethyl)cyclohexane is isolated as a light yellow oil.

EXAMPLE 40

Production of (1S,2R)-1-amino-2-(benzoyloxymethyl)cyclohexane by Lossen Rearrangement of (1S,2R)-2-hydroxymethyl-1-cyclohexanecarboxylate hydroxamic acid Ten grams of (2R,3S)-2-methyl-3 hydroxybutyrohydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (1S,2R)-1-amino-2-(benzoyloxymethyl)cydohexane is isolated as a light yellow solid.

EXAMPLE 41

Production of (1S,2R)-1-amino-2-(hydroxymethyl) cyclohexane by Curtius Rearrangement of (1S,2R)-2-hydroxymethyl-1-cyclohexanecarboxylate hydrazide The hydrazide of (1S,2R)-2-hydroxymethyl-1-cyclohexanecarboxylic acid (0.5 gram) is reacted with a solution of 0.5 grams of sodium nitrite in 10 ml of 5% $H_2SO_4$. The reaction mixture is maintained for 1 hour at 0–5° C, followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (1S,2R)-1-amino-2-(hydroxymethyl)cyclohexane is isolated as a light yellow

EXAMPLE 42

Production of (1S,2R)-1-amino-2-(hydroxymethyl) cyclopentane by Hofmann Rearrangement of (1S, 2R)-2-hydroxymethyl-1-cyclopentanecarboxamide Ten grams of (1S,2R)-2-hydroxymethyl-1-cyclopentanecarboxamide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (1S,2R)-1-amino-2-(hydroxymethyl)cyclopentane is isolated as a light yellow oil.

EXAMPLE 43

Production of (1S,2R)-1-amino-2-(benzoyloxymethyl)cydopentane by Lossen Rearrangement of (1S,2R)-2-hydroxymethyl-1-cyclopentanecarboxylate hydroxamic acid Ten grams of (1S,2R)-2-hydroxymethyl-1-cydopentanecarboxylate hydroxarnic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (1S,2R)-1-amino-2-(benzoyloxymethyl) cydopentane is isolated as a light yellow solid.

EXAMPLE 44

Production of (1S,2R)-1-amino-2-(hydroxymethyl) cydopentane by Curtius Rearrangement of (1S,2R)-2-hydroxymethyl-1-cyclohexanecarboxylate hydrazide The hydrazide of (1S,2R)-2-hydroxymethyl-1-cyclohexanecarboxylic acid (0.5 gram) is reacted with a solution of 0.5 grams of sodium nitrite in 10 ml of 5% $H_2SO_4$. The reaction mixture is maintained for 1 hour at 0–5° C, followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (1S,2R)-1-amino-2-(hydroxymethyl)cyclopentane is isolated as a light yellow oil.

EXAMPLE 45

Production of (2S,3S)-2-methyl-3-aminobutanol by Hofmann Rearrangement of (2S,3R)-2,3-dimethyl-4-hydroxybutyramide Ten grams of (2S,3R)-2,3-dimethyl-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (2S,3S)-2-methyl-3-aminobutanol is isolated as a light yellow oil.

EXAMPLE 46

Production of (2S,3S)-2-methyl-3-aminobutanol benzoate ester by Lossen Rearrangement of (2S, 3R)-2,3-dimethyl-4-hydroxybutanoic hydroxamic acid Ten grams of (2S,3R)-2,3-dimethyl-4-hydroxybutanoic hydroxamic acid is reacted with 10 grams of benzoyl chloride under Schotten-Bauman conditions, followed by wanming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (2S,3S)-2-methyl-3-aminobutanol benzoate ester is isolated as a light yellow solid.

EXAMPLE 47

Production of (2S,3S)-2-methyl-3-aminobutanol by Curtius Rearrangement of (2S,3R)-2,3-dimethyl-4-hydroxybutanoic acid hydrazide The hydrazide of (2S,3R)-2,3-dimethyl-4-hydroxybutanoic acid (0.5 gram) is reacted with a solution of 0.5 grams of sodium nitrite in 10 ml of 5% $H_2SO_4$. The reaction mixture is maintained for 1 hour at 0–5° C, followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (2S,3S)-2-methyl-3-aminobutanol is isolated as a light yellow oil.

EXAMPLE 48

Production of (R)-1-phenyl-3-hydroxypropylamine by Hofmann Rearrangement of (R)-2-phenyl-4-hydroxybutyramide Ten grams of (R)-2-phenyl-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (R)-1-phenyl-3-hydroxypropylamine is isolated as a light yellow oil.

EXAMPLE 49

Production of (R)-1-phenyl-3-hydroxypropylamine benzoate ester by Lossen Rearrangement of (R)-2-phenyl-4-hydroxybutanoic hydroxamic acid Ten grams of (R)-2-phenyl-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (R)-1-phenyl-3-hydroxypropylamine benzoate ester is isolated as a light yellow solid.

EXAMPLE 50

Production of (R)-1-phenyl-3-hydroxypropylamine by Curtius Rearrangement of (R)2-phenyl-4-hydroxybutanoic acid hydrazide The hydrazide of (R)-2-phenyl-4-hydroxybutanoic acid (0.5 gram) is reacted with a solution of 0.5 grams of sodium nitrite in 10 ml of 5% $H_2SO_4$. The reaction mixture is maintained for 1 hour at 0–5° C, followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (R)-1-phenyl-3-hydroxypropylamine is isolated as a light yellow oil.

EXAMPLE 51

Production of (S)-1-phenyl-3-hydroxypropylamine by Hofmann Rearrangement of (S)-2-phenyl-4-hydroxybutyramide Ten grams of (S)-2-phenyl-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (S)-1-phenyl-3-hydroxypropylamine is isolated as a light yellow oil.

EXAMPLE 52

Production of (S)-1-phenyl-3-hydroxypropylamine benzoate ester by Lossen Rearrangement of (S)-2-phenyl-4-hydroxybutanoic hydroxamic acid Ten grams of (S)-2-phenyl-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (S)-1-phenyl-3-hydroxypropylamine benzoate ester is isolated as a light yellow solid.

EXAMPLE 53

Production of (S)-1-phenyl-3-hydroxypropylamine by Curtius Rearrangement of (S)2-phenyl-4-hydroxybutanoic acid hydrazide The hydrazide of (S)-2-phenyl-4-hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (S)-1-phenyl-3-hydroxypropylamine is isolated as a light yellow oil.

EXAMPLE 54

Production of (R)-1-benzyl-3-hydroxypropylamine by Hofmann Rearrangement of (R)-2-benzyl-4-hydroxybutyramide Ten grams of (R)-2-benzyl-4hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (R)-1-benzyl-3hydroxypropylamine is isolated as a light yellow oil.

EXAMPLE 55

Production of (R)-1-benzyl-3hydroxypropylamine benzoate ester by Lossen Rearrangement of (R)-2-benzyl-4-hydroxybutanoic hydroxamic acid Ten grams of (R)-2-benzyl-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (R)-1-benzyl-3-hydroxypropylamine benzoate ester is isolated as a light yellow solid.

EXAMPLE 56

Production of (R)-1-benzyl-3-hydroxypropylamine by Curtius Rearrangement of (R)2-benzyl-4-hydroxybutanoic acid hydrazide The hydrazide of (R)-2-benzyl-4hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (R)-1-benzyl-3-hydroxypropylamine is isolated as a light yellow oil.

EXAMPLE 57

Production of (S)-1-benzyl-3-hydroxypropylamine by Hofmann Rearrangement of (S)-2-benzyl-4-hydroxybutyramide Ten grams of (S)-2-benzyl-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (S)-1-benzyl-3-hydroxypropylamine is isolated as a light yellow oil.

EXAMPLE 58

Production of (S)-1-benzyl-3-hydroxypropylamine benzoate ester by Lossen Rearrangement of (S)-2-benzyl-4-hydroxybutanoic hydroxamic acid Ten grams of (S)-2-benzyl-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (S)-1-benzyl-3-hydroxypropylamine benzoate ester is isolated as a light yellow solid.

EXAMPLE 59

Production of (S)-1-benzyl-3-hydroxypropylamine by Curtius Rearrangement of (S)2-benzyl-4-hydroxybutanoic acid hydrazide The hydrazide of (S)-2-benzyl-4-hydroxybutanoic acid (0.5 gram) is reacted with a solution of 0.5 grams of sodium nitrite in 10 ml of 5% $H_2SO_4$. The reaction rnixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (S)-1-benzyl-3-hydroxypropylamine is isolated as a light yellow oil.

EXAMPLE 60

Production of (R)-1-(4fluorophenyl)-3-hydroxypropylamine by Hofmann Rearrangement of (R)-2-(4-fluorophenyl)-4-hydroxybutyramide Ten grams of (R)-2-(4-fluorophenyl)-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (R)-1-(4-fluorophenyl)-3-hydroxypropylamine is isolated as a light yellow oil.

EXAMPLE 61

Production of (R)-1-(4-fluorophenyl)-3-hydroxypropylamine benzoate ester by Lossen Rearrangement of (R)-2-(4-fluorophenyl)-4-hydroxybutanoic hydroxamic acid Ten grams of (R)-2-(4-fluorophenyl)-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (R)-1-(4-fluorophenyl)-3-hydroxypropylamine benzoate ester is isolated as a light yellow solid.

EXAMPLE 62

Production of (R)-1-(4-fluorophenyl)-3-hydroxypropylamine by Curtius Rearrangement of (R)-2-(4-fluorophenyl)-4-hydroxybutanoic acid hydrazide The hydrazide of (R)-2-(4fluorophenyl)-4-hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (R)-1-(4-fluorophenyl)-3-hydroxypropylamine is isolated as a light yellow oil.

EXAMPLE 63

Production of (S)-1-(4-fluorophenyl)-3-hydroxypropylamine by Hofmann Rearrangement of (S)-2-(4-fluorophenyl)-4-hydroxybutyramide Ten grams of (S)-2-(4-fluorophenyl)-4-hydroxybutyramide was dissolved in 250 ml of 0.03 M NaOH and added slowly to a solution 25 grams of bromine in 300 ml of 0.03 M NaOH. The mixture was warmed with stirring until the reddish brown color disappeared. The solution was then cooled, extracted with methyl t-butyl ether ×250 ml), and the extracts dried over $MgSO_4$, filtered, and the solvent removed by rotary evaporation. The product (S)-1-(4-fluorophenyl)-3-hydroxypropylamine is isolated as a light yellow oil.

EXAMPLE 64

Production of (S)-1-(4-fluorophenyl)-3-hydroxypropylamine benzoate ester by Lossen Rearrangement of (S)-2-(4fluorophenyl)-4-hydroxybutanoic hydroxamic acid Ten grams of (S)-2-(4-fluorophenyl)-4-hydroxybutanoic hydroxamic acid is reacted with 10 grams of benzoyl chloride under Schotten-Bauman conditions, followed by warming to reflux. Reaction progress is monitored by thin layer chromatography. The solution is then cooled to room temperature, extracted with methyl t-butyl ether ×250 ml), and the extracts dried over $MgSO_4$, filtered, and the solvent removed by rotary evaporation. The product (S)-1-(4-fluorophenyl)-3-hydroxypropylamine benzoate ester is isolated as a light yellow solid.

EXAMPLE 65

Production of (S)-1-(4-fluorophenyl)-3-hydroxypropylamine by Curtius Rearrangement of (S)-2-(4-fluorophenyl)-4-hydroxybutanoic acid hydrazide The hydrazide of (S)-2-(4-fluorophenyl)-4-hydroxybutanoic acid (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (S)-1-(4fluorophenyl)-3-hydroxypropylamine is isolated as a light yellow oil.

What is claimed is:

1. A method for producing chiral 1,3-aminoalcohols which comprises:

a) the stereoselective oxidation of a 1,4-diol selected from the group consisting of

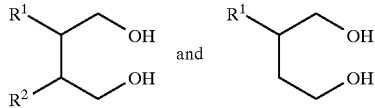

wherein $R^1$ and $R^2$ are independently chosen from the group consisting of alkyl, alkenyl, cydoalkyl, cydoalkylalkyl, cydoalkenyl, cydoalkenylalkyl, alkynyl, aryl, aralkyl, aralkenyl, heterocyclic ring system, or $R^1$ and $R^2$ together form a cydoalkyl, cydoalkenyl, aryl, or heterocyclic ring system to a chiral gamma-lactone catalyzed by an alcohol dehydrogenase, b) treatment of the chiral gamma-lactone of step (a) with ammonia, hydroxylamine, or hydrazine under conditions permitting the conversion of the lactone to the corresponding amide, hydroxamic acid, or hydrazide derivative, c) exposing the 4-hydroxyamide, 4-hydroxyhydroxamic acid, or 4-hydroxyhydrazide produced in step (b) to conditions permitting stereospecific rearrangement to the corresponding chiral 1,3-aminoalcohol, and optionally, d) recovering the resulting chiral 1,3-aminoalcohol.

2. The method of claim 1 in which the source of the dehydrogenase is a microorganism.

3. The method of claim 1 in which the alcohol dehydrogenase is selected from the group consisting of yeast alcohol dehydrogenase, horse liver alcohol dehydrogenase, *Thermoanaerobium brockii* alcohol dehydrogenase, *Lactobacillus kefir* alcohol dehydrogenase.

4. The method of claim 1 in which the nicotinamide cofactor for the dehydrogenase is recycled.

5. The method of claim 1 in which the conversion of the gamma-lactone to the corresponding amide, hydroxamic add or hydrazide derivative is catalyzed by an esterase, lipase, protease, or amidase.

6. A method for producing esters of chiral 1,3-aminoalcohols which comprises:

a) the stereoselective oxidation of a 1,4-diol selected from the group consisting of

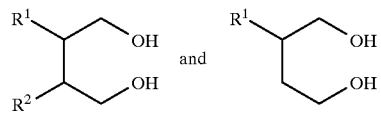

wherein $R^1$ and $R^2$ are independently chosen from the group consisting of alkyl, alkenyl, cydoalkyl, cydoalkylalkyl, cydoalkenyl, cydoalkenylalkyl, alkynyl, aryl, aralkyl, aralkenyl, heterocyclic ring system, or $R^1$ and $R^2$ together form a cycloalkyl, cycloalkenyl, aryl, or heterocyclic ring system to a chiral gamma-lactone catalyzed by an alcohol dehydrogenase, b) treatment of the chiral gamma-lactone of step (a) with hydroxylamine under conditions permitting the conversion of the gamma-lactone to the corresponding hydroxamic acid derivative, c) exposing the 4-hydroxyhydroxamic acid produced in step (b) to conditions of the Lossen rearrangement in which an acyl chloride is used to bring about the stereospecific rearrangement of the hydroxamic acid, producing an ester of a chiral 1,3-aminoalcohol, and optionally, d) recovering the ester of the chiral 1,3-aminoalcohol.

7. The method of claim 6 in which the source of the dehydrogenase is a microorganism.

8. The method of claim 6 in which the alcohol dehydrogenase is selected from the group consisting of yeast alcohol dehydrogenase, horse liver alcohol dehydrogenase, *Thermoanaerobium brockii* alcohol dehydrogenase, *Lactobacillus kefir* alcohol dehydrogenase.

9. The method of claim 6 in which the nicotinamide cofactor for the dehydrogenase is recycled.

10. The method of claim 6 in which the conversion of the gamma-lactone to the corresponding hydroxamic acid is catalyzed by an esterase, lipase, protease, or amidase.

11. A method for producing chiral 1,3-aminoakohols which comprises a) producing an ester of a chiral 1,3-aminoalcohol using the method described in claims 6, 7, 8, 9, or 10 and b) hydrolyzing the ester produced in step (a).

* * * * *

UNITED STATES PATENT AND TRADEMARK OFFICE
CERTIFICATE OF CORRECTION

PATENT NO. : 5,916,786
DATED : June 29, 1999
INVENTOR(S) : J. David Rozzell, Jr.

It is certified that error appears in the above-identified patent and that said Letters Patent is hereby corrected as shown below:

Column 3,
Line 17, replace "1,2-cydopentane" with -- 1,2-cyclopentane --.
Line 41, replace "sulfhiydryl" with -- sulfhydryl --.
Line 55, replace "cydoalkyl" with -- cycloalkyl --.
Line 56, replace "cydobutyl, cydopentyl, cydohexyl, cydoheptyl" with -- cyclobutyl, cyclopentyl, cyclohexyl, cycloheptyl --.
Line 57, replace "3-methylcydohexyl" with -- 3-methylcyclohexyl --.
Line 67, replace "cydohexenyl" with -- cyclohexenyl --.

Column 4,
Line 1, replace "cydoheptenyl, 2-methylcydopentenyl" with -- cycloheptenyl, 2-methylcyclopentenyl --.
Line 2, replace "3-chlorocydohexenyl" with -- 3-chlorocyclohexenyl --.
Line 12, replace "cydopropyl, cydobutyl" with -- cyclopropyl, cyclobutyl --.
Line 20, replace "cydoalkenyl" with -- cycloalkenyl --.
Line 25, replace "cydoalkyl" and "cydopropenyl" with -- cyclolkyl -- and -- cyclopropenyl --.
Line 26, replace "cydobutenyl, cydopentenyl" and "cydopropenyl" with -- cyclobutenyl, cyclopentenyl -- and -- cyclopropenyl --.
Line 27, replace "2-methylcydopentenyl" with -- 2-methylcyclopentenyl --.
Line 30, replace "3-nitrocydohexenyl" with -- 3-nitrocyclohexenyl --.
Line 45, replace "carbocydic" with -- carbocyclic --.

Column 5,
Line 5, replace "sulffiydryl" with -- sulfhydryl --.
Line 9, replace "phthanmidoyl" with -- phthalimidoyl --.
Line 31, replace "dinudeotide" with -- dinucleotide --.
Line 43, replace "T. Takarnura" with -- T. Takamura --.

Column 6,
Line 51, replace "4-hydroxyhydroxamic add" with -- 4-hydroxyhydroxamic acid --.
Line 52, replace "4hydroxyamide, 4hydroxyhydroxamic" and "4hydroxyhydrazide" with -- 4-hydroxyamide, 4-hydroxyhydroxamic -- and -- 4-hydroxyhydrazide --.
Line 58, replace "hydroxamic add" with -- hydroxamic acid --.

UNITED STATES PATENT AND TRADEMARK OFFICE
CERTIFICATE OF CORRECTION

PATENT NO. : 5,916,786
DATED : June 29, 1999
INVENTOR(S) : J. David Rozzell, Jr.

It is certified that error appears in the above-identified patent and that said Letters Patent is hereby corrected as shown below:

Column 7,
Line 50, replace "pp. 397-05" with -- pp. 397-405 --.
Line 67, replace "1,2-cydohexane" with -- 1,2-cyclohexane --.

Column 8,
Line 21, replace "dear" with -- clear --.

Column 9,
Line 20, replace "mononudeotide" with -- mononucleotide --.
Line 21, replace "dear" with -- clear --.
Line 50, replace "βNAD+" with -- β-NAD+ --.

Column 10,
Line 8, replace "Cis-1,2-cydopentane" with -- Cis-1,2-cyclopentane --.
Line 12, replace "dear" with -- clear --.
Line 40, replace "Cis-1,2-cydopentane" with -- Cis-1,2-cyclopentane --.
Line 61, replace "6one" with -- 6-one --.

Column 13,
Line 7, replace "cydohexylbutyrolactone" with -- cyclohexylbutyrolactone --.
Line 11, replace "2-Cydohexyl" with -- 2-Cyclohexyl --.
Line 31, replace "cydohexylbutyrolactone" with -- cyclohexylbutyrolactone --.

Column 15,
Lines 22,34, replace "cydohexanecarboxylate" with -- cyclohexanecarboxylate -- (both occurrences).
Line 38, replace "hydroxamic add" with -- hydroxamic acid --.
Line 41, replace "oxabicylo" with -- oxaicyclo --.
Line 56, replace "oxabicylo" with -- oxabicyclo --.

Column 16,
Line 10, replace "oxabicylo" with -- oxabicyclo --.
Line 21, replace "cydopentanecarboxylate" with -- cyclopentanecarboxylate --.
Line 63, replace "cydohexanecarboxylic" with -- cyclohexanecarboxylic --.

UNITED STATES PATENT AND TRADEMARK OFFICE
CERTIFICATE OF CORRECTION

PATENT NO.   : 5,916,786
DATED        : June 29, 1999
INVENTOR(S)  : J. David Rozzell, Jr.

It is certified that error appears in the above-identified patent and that said Letters Patent is hereby corrected as shown below:

Column 17,
Line 8, replace "cydohexanecarboxylate" with -- cyclohexanecarboxylate --.
Line 13, replace "cydopentanecarboxylic" with -- cyclopentanecarboxylic --.

Column 18,
Line 10, replace "cydopentanecarboxamide" with -- cyclopentanecarboxamide --.
Line 44, replace "4hydroxybutyramide" with 4-hydroxbutyramide.

Column 20,
Line 63, replace "cydohexane" with -- cyclohexane --.

Column 21,
Line 24, replace "cydohexane" with -- cyclohexane --.
Line 43, after "yellow" insert -- oil. --.
Line 63, replace "cydopentane" with -- cyclopentane --.
Line 67, replace "cydopentanecarboxylate" with -- cyclopentanecarboxylate --.

Column 22,
Line 8, replace "cydopentane" with -- cyclopentane --.
Line 13, replace "cydopentane" with -- cyclopentane --.
Line 53, replace "wanming" with -- warming --.

Column 25,
Line 6, replace "4hydroxybutanoic" with -- 4-hydroxybutanoic --.

Column 27,
Lines 39,40, replace "cydoalkyl, cydoalkylalkyl, cydoalkenyl, cydoalkenylalkyl with" -- cycloalkyl, cycloalkylalkyl, cycloalkenyl, cycloalkenylalkyl --.
Line 42, replace "cydoalkyl, cydoalkenyl" with -- cycloalkyl, cycloalkenyl --.

UNITED STATES PATENT AND TRADEMARK OFFICE
CERTIFICATE OF CORRECTION

PATENT NO. : 5,916,786
DATED : June 29, 1999
INVENTOR(S) : J. David Rozzell, Jr.

It is certified that error appears in the above-identified patent and that said Letters Patent is hereby corrected as shown below:

Column 28,
Line 7, replace "hydroxamic add" with -- hydroxamic acid --.
Lines 23,24, replace "cydoalkyl, cydoalkylalkyl, cydoalkenyl, cydoalkenylalkyl" with -- cycloalkyl, cycloalkylalkyl, cycloalkenyl, cycloalkenylalkyl --.
Line 53, replace "aminoakohols" with -- aminoalcohols --.

Signed and Sealed this

Eleventh Day of September, 2001

Attest:

NICHOLAS P. GODICI
*Attesting Officer*   *Acting Director of the United States Patent and Trademark Office*